US010702243B2

(12) United States Patent
Yang et al.

(10) Patent No.: US 10,702,243 B2
(45) Date of Patent: Jul. 7, 2020

(54) ULTRASOUND DIAGNOSIS APPARATUS, WEARABLE DEVICE, METHOD OF CONTROLLING ULTRASOUND DIAGNOSIS APPARATUS, METHOD OF CONTROLLING WEARABLE DEVICE, AND RECORDING MEDIUM HAVING METHODS RECORDED THEREON

(71) Applicant: SAMSUNG MEDISON CO., LTD., Hongcheon-gun (KR)

(72) Inventors: Sun-mo Yang, Hongcheon-gun (KR); Jin-hwan Park, Hongcheon-gun (KR); Jun-sang Yoo, Hongcheon-gun (KR); Kwang-hee Lee, Hongcheon-gun (KR); Seung-ju Lee, Hongcheon-gun (KR); Yoon-gu Hwang, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 430 days.

(21) Appl. No.: 14/819,569

(22) Filed: Aug. 6, 2015

(65) Prior Publication Data
US 2016/0183918 A1    Jun. 30, 2016

(30) Foreign Application Priority Data
Dec. 31, 2014  (KR) .................. 10-2014-0195954

(51) Int. Cl.
*A61B 8/00*  (2006.01)
*A61B 8/14*  (2006.01)
*A61B 8/08*  (2006.01)

(52) U.S. Cl.
CPC .............. *A61B 8/462* (2013.01); *A61B 8/14* (2013.01); *A61B 8/461* (2013.01); *A61B 8/486* (2013.01);
(Continued)

(58) Field of Classification Search
CPC ........... A61B 8/00; A61B 8/462; A61B 8/565; A61B 8/461; A61B 8/486; A61B 8/488;
(Continued)

(56) References Cited

U.S. PATENT DOCUMENTS 4,890,624 A * 1/1990 Ganguly .................. A61B 8/02
600/453
4,984,576 A * 1/1991 Schulenberg ............ A61B 8/02
600/453
(Continued)

FOREIGN PATENT DOCUMENTS

CN    203506759 U    4/2014
JP    2009-519739 A   5/2009
(Continued)

OTHER PUBLICATIONS

Communication dated Jun. 3, 2016 issued by the European Patent Office in counterpart European Patent Application No. 15176197.0.
(Continued)

*Primary Examiner* — Luther Behringer
*Assistant Examiner* — Sean D Mattson
(74) *Attorney, Agent, or Firm* — Sughrue Mion, PLLC

(57) ABSTRACT

An ultrasound diagnosis apparatus including: an image processor configured to acquire ultrasound data of an object; a controller configured to generate a wearable signal carrying information corresponding to a difference between the acquired ultrasound data and reference ultrasound data; and a communication module configured to transmit the wearable signal to a wearable device. The wearable signal is acquired by comparing the ultrasound data with the reference ultrasound data and includes information about the difference between the ultrasound data and the reference ultrasound data.

18 Claims, 14 Drawing Sheets

(52) U.S. Cl.
CPC ............... *A61B 8/488* (2013.01); *A61B 8/56* (2013.01); *A61B 8/565* (2013.01)

(58) Field of Classification Search
CPC .... A61B 8/56; A61B 8/14; A61B 8/40; G01S 7/00; G08B 21/02
See application file for complete search history.

(56) References Cited

U.S. PATENT DOCUMENTS

| | | | | |
|---|---|---|---|---|
| 5,069,218 | A * | 12/1991 | Ikeda | A61B 5/02411 600/453 |
| 5,246,006 | A * | 9/1993 | Kanda | A61B 8/06 600/441 |
| 6,610,012 | B2 * | 8/2003 | Mault | A61B 5/0011 600/300 |
| 7,547,282 | B2 | 6/2009 | Lo et al. | |
| 8,260,405 | B2 | 9/2012 | Aarts | |
| 2002/0067359 | A1 * | 6/2002 | Brodsky | A61B 8/546 345/440 |
| 2003/0125629 | A1 * | 7/2003 | Ustuner | A61B 8/00 600/459 |
| 2005/0080329 | A1 * | 4/2005 | Uchibori | A61B 8/06 600/407 |
| 2005/0222506 | A1 * | 10/2005 | Takimoto | A61B 8/06 600/455 |
| 2007/0130287 | A1 * | 6/2007 | Kumar | A61N 1/08 709/217 |
| 2009/0069642 | A1 * | 3/2009 | Gao | A61B 5/02055 600/300 |
| 2010/0262006 | A1 * | 10/2010 | Kasahara | A61B 8/02 600/443 |
| 2010/0274145 | A1 * | 10/2010 | Tupin, Jr. | A61B 5/0444 600/511 |
| 2013/0158407 | A1 * | 6/2013 | Kabakov | A61B 8/02 600/453 |
| 2013/0184583 | A1 * | 7/2013 | Yao | A61B 8/4444 600/441 |
| 2014/0343427 | A1 * | 11/2014 | Fukunaga | A61B 8/0883 600/440 |
| 2015/0216509 | A1 | 8/2015 | Yamagata et al. | |

FOREIGN PATENT DOCUMENTS

| | | |
|---|---|---|
| KR | 10-2007-0114541 A | 12/2007 |
| KR | 10-1354625 B1 | 1/2014 |
| KR | 10-2014-0045055 A | 4/2014 |
| WO | 2014/054810 A1 | 4/2014 |

OTHER PUBLICATIONS

Communication dated Jan. 16, 2018, issued by the European Patent Office in counterpart European Patent Application No. 15176197.0.

* cited by examiner

ULTRASOUND DIAGNOSIS APPARATUS, WEARABLE DEVICE, METHOD OF CONTROLLING ULTRASOUND DIAGNOSIS APPARATUS, METHOD OF CONTROLLING WEARABLE DEVICE, AND RECORDING MEDIUM HAVING METHODS RECORDED THEREON

RELATED APPLICATION

This application claims the benefit of Korean Patent Application No. 10-2014-0195954, filed on Dec. 31, 2014, in the Korean Intellectual Property Office, the disclosure of which is incorporated herein in its entirety by reference.

BACKGROUND

1. Field

One or more exemplary embodiments relate to an ultrasound diagnosis apparatus, a method of controlling the ultrasound diagnosis apparatus, a wearable device for transmitting or receiving data to or from the ultrasound diagnosis apparatus, and a method of controlling the wearable device.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to no radiation exposure, compared to X-ray apparatuses. Therefore, an ultrasound diagnosis apparatus is widely used together with other types of imaging diagnosis apparatus including a computed tomography (CT) apparatus, a magnetic resonance imaging (MRI) apparatus, and the like Wearable devices refer to all types of electronic devices that are worn on the body to perform computing tasks. Since wearable devices communicate with a user near the user, they have various advantages and are being actively developed all over the world. Examples of wearable devices include a digital armband for checking a user's health and fitness status, a smartwatch that incorporates the functionality of a smartphone into an actual watch, and smart glasses that combine eye glasses with a smartphone. Due to their benefits, there is demand for wearable devices in the field of medical equipment.

SUMMARY

One or more exemplary embodiments include an ultrasound diagnosis apparatus and a method of controlling the ultrasound diagnosis apparatus and a wearable device and a method of controlling the wearable device, which allow a user to easily recognize information that is generated based on a signal acquired by the ultrasound diagnosis apparatus through the wearable device via which the information is output.

Additional aspects will be set forth in part in the description which follows and, in part, will be apparent from the description, or may be learned by practice of the presented exemplary embodiments.

According to one or more exemplary embodiments, an ultrasound diagnosis apparatus includes: an image processor configured to acquire ultrasound data of an object; a controller configured to generate a wearable signal carrying information corresponding to a difference between the acquired ultrasound data and reference ultrasound data; and a communication module configured to transmit the wearable signal to a wearable device.

The acquired ultrasound data may include ultrasound Doppler data, and the controller may compare first Doppler spectrum data corresponding to the ultrasound Doppler data with second Doppler spectrum data corresponding to the reference ultrasound data, thereby generating the wearable signal based on differences between values of the first and second Doppler spectrum data.

The controller may adjust the intensity of the wearable signal based on the differences between the values of the first and second Doppler spectrum data.

The controller may adjust the intensity of the wearable signal based on differences between peak values.

The controller may determine an item requiring examination of the object based on the differences between the peak values and control the wearable device to display the determined item.

If at least one of the differences between the peak values exceeds a predetermined reference value, the controller may control the wearable device to generate an alarm.

The image processor may acquire ultrasound Doppler data of the object, and the controller may compare a period in a first graph representing a Doppler spectrum corresponding to the acquired ultrasound Doppler data with a period in a second graph representing a Doppler spectrum obtained from predetermined ultrasound data and, if a difference between the periods in the first and second graphs exceeds a predetermined reference value, control the wearable device to generate an alarm.

The image processor may acquire ultrasound color data of the object, and the controller may compare the acquired ultrasound color data with predetermined ultrasound color data, thereby generating a wearable signal based on a difference in color between the acquired ultrasound color data and the predetermined ultrasound color data.

Based on the difference in color, the controller may control the wearable device to display the acquired ultrasound color data in a color corresponding to the difference in color.

If a value corresponding to the difference in color is greater than a predetermined reference value, the controller may control the wearable device to generate an alarm.

The reference ultrasound data may include standard ultrasound data and history ultrasound data of the object.

The ultrasound diagnosis apparatus may further include a wearable device configured to receive the wearable signal transmitted from the communication module, convert the wearable signal into at least one selected from the intensity of vibration, variation in color, and strength of sound, and output the at least one result obtained by the conversion.

According to one or more exemplary embodiments, a wearable device includes: a communication module configured to receive a wearable signal carrying information corresponding to a difference between acquired ultrasound data and reference ultrasound data; and an output unit configured to output a user interface signal corresponding to the difference based on the wearable signal.

The output unit may include a vibration motor configured to output, based on the difference, a vibration that has varying intensity according to the wearable signal.

The output unit may include a display configured to output, based on the difference, a screen depicting the wearable signal as a variation in color.

The output unit may further include an audio output unit configured to output, based on the difference, an audio signal representing the wearable signal as strength of sound.

According to one or more exemplary embodiments, a method of controlling an ultrasound diagnosis apparatus includes: acquiring ultrasound data of an object; generating a wearable signal carrying information corresponding to a difference between the acquired ultrasound data and reference ultrasound data; and transmitting the wearable signal to a wearable device.

According to the one or more exemplary embodiments, a user may easily determine a status of an object by sensing the status through the skin or vision by comparing ultrasound data of an object against reference data via a wearable device.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
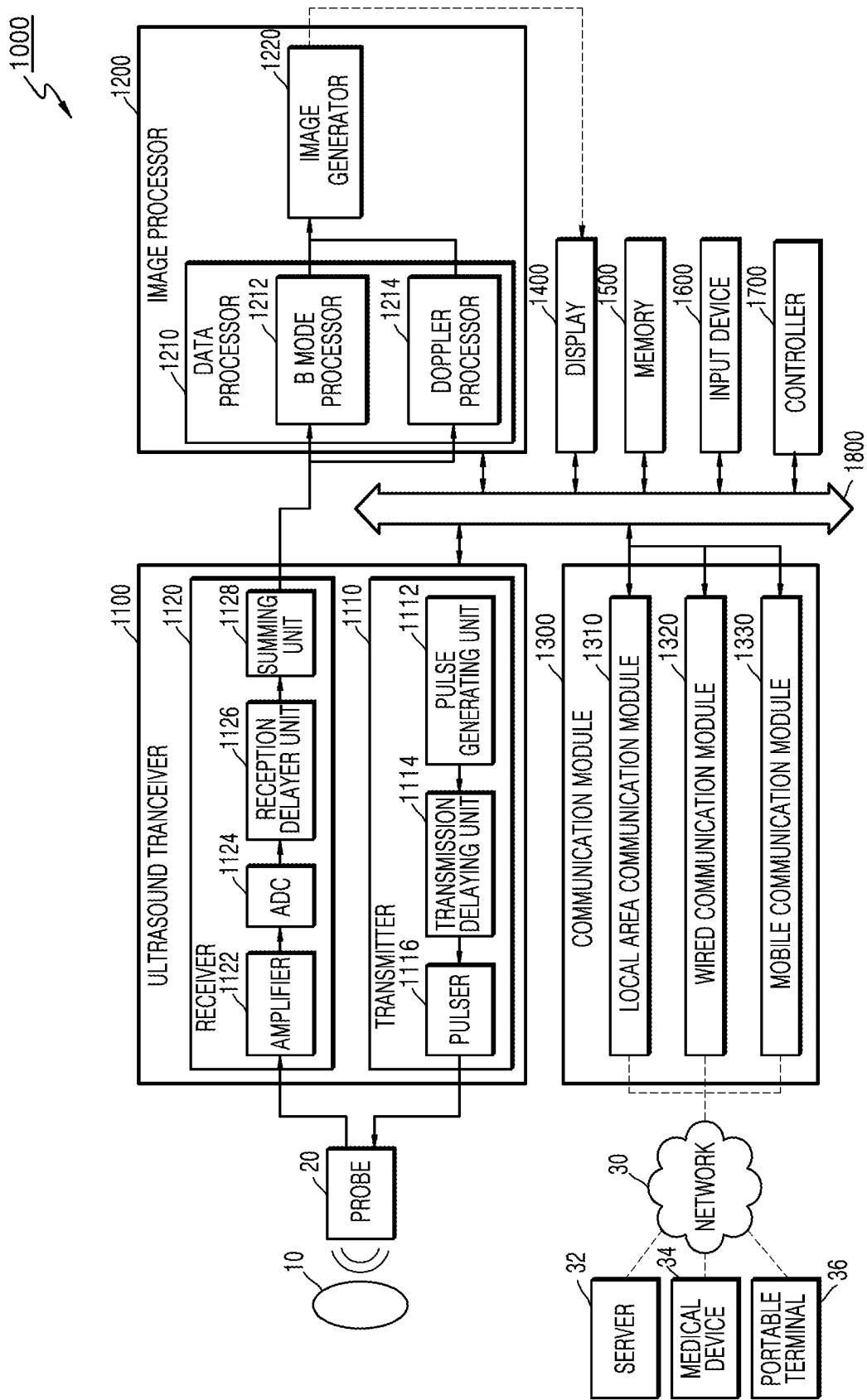
FIG. 1 is a block diagram of a configuration of an ultrasound diagnosis apparatus according to an exemplary embodiment.

Reference will now be made in detail to exemplary embodiments, examples of which are illustrated in the accompanying drawings, wherein like reference numerals refer to like elements throughout. The exemplary embodiments are not intended to limit the present disclosure but to aid in the understanding of implementation of the embodiments. In the present description, well-known functions and components will not be described so as not to unnecessarily obscure the essence of the present disclosure. Expressions such as "at least one of," when preceding a list of elements, modify the entire list of elements and do not modify the individual elements of the list.

Hereinafter, the terms used in the specification will be briefly described, and then the present disclosure will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the present disclosure.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments will be described in detail with reference to the figures.

FIG. 1 is a block diagram showing a configuration of an ultrasound diagnosis apparatus 1000 according to an embodiment of the present disclosure. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 1120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform. Furthermore, an M mode ultrasound image may be a grayscale image or Doppler image obtained by scanning an object in an M mode.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

The display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1700. However, embodiments of the present invention are not limited thereto.

Figure 2:
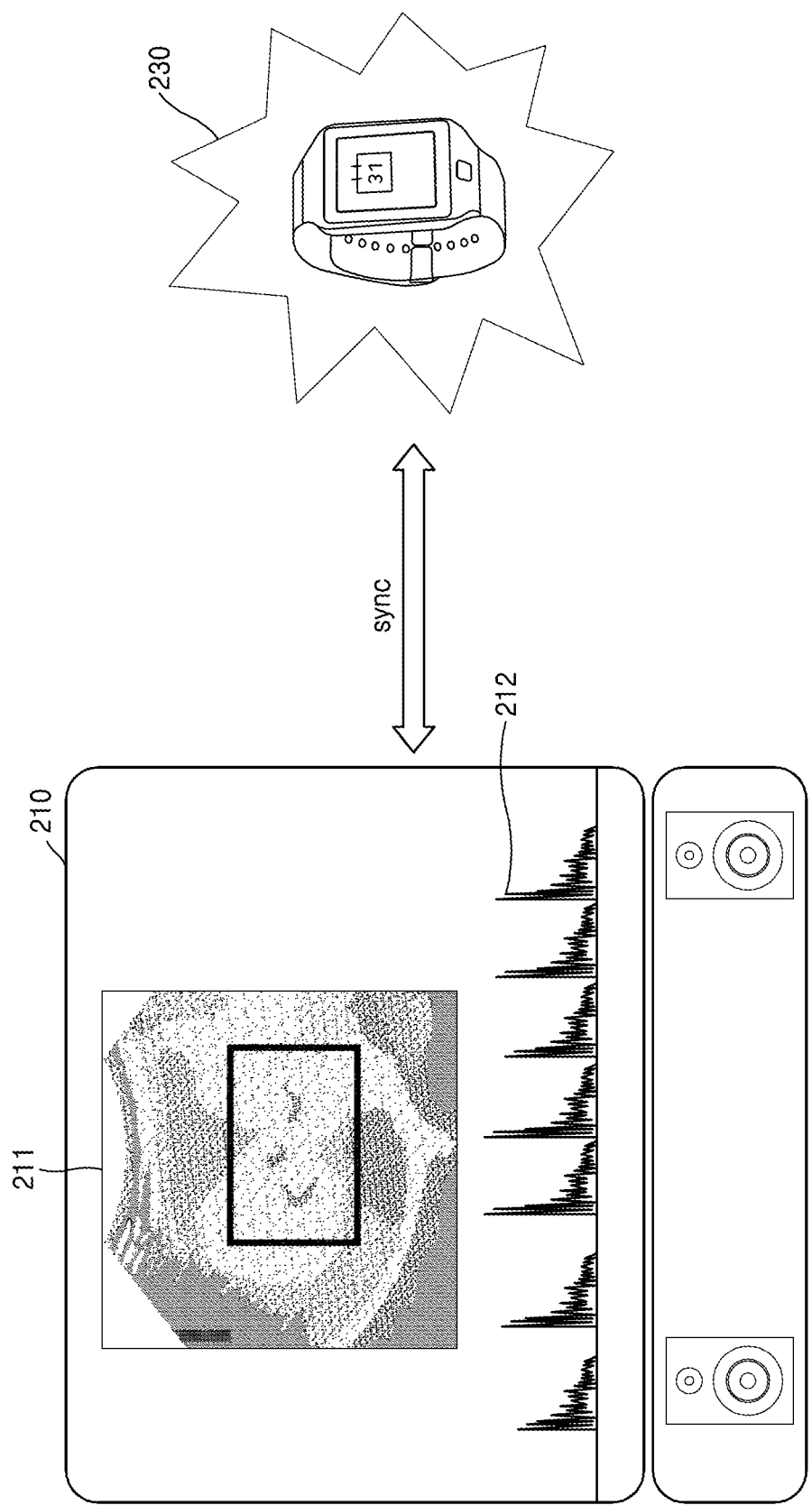
FIG. 2 is a diagram for explaining representation of ultrasound Doppler data via a wearable device.

FIG. 2 is a diagram for explaining an output of ultrasound Doppler data via a wearable device 230. FIG. 2 shows an ultrasound image 211 and an ultrasound Doppler spectrum 212.

The image processor 1200 may generate the ultrasound image 211 and the ultrasound Doppler spectrum 212 based on ultrasound echo signals acquired via the probe 20. The ultrasound image 211 and the ultrasound Doppler spectrum 212 may generally be represented via a screen 210 of an ultrasound diagnosis apparatus (e.g., the ultrasound diagnosis apparatus 1000 of FIG. 1) or be provided to a user via a speaker (not shown) of the ultrasound diagnosis apparatus.

An ultrasound diagnosis apparatus according to an exemplary embodiment may provide a signal generated therein to a user via the wearable device 230. The signal generated in the ultrasound diagnosis apparatus may include ultrasound Doppler data and ultrasound color data. A signal detected by the ultrasound diagnosis apparatus may include a biosignal such as an electrocardiogram (ECG) signal.

The wearable device 230 may be in the form of a smartwatch, smart glasses, a ring, a smartphone, and a personal digital assistant (PDA), but is not limited thereto.

Furthermore, according to an exemplary embodiment, the ultrasound diagnosis apparatus may adjust the intensity of provision of a signal generated therein such as the intensity of vibration, sound loudness, and brightness while transmitting the signal to the wearable device 230. For example, an ultrasound image may be represented the same on the wearable device 230 as on the ultrasound diagnosis apparatus, but the intensity of vibration or sound from the wearable device 230 may be adjusted. Thus, according to an exemplary embodiment, a signal that can be distinguished by a user in more ways than an image may be provided intuitively to a user, thus allowing the user to intuitively recognize a user interface signal that would otherwise not be recognized via the screen 210 of the ultrasound diagnosis apparatus. In this case, the user interface signal may be a signal that can be recognized through at least one of visual, auditory, and tactile senses and provided for the user to recognize predetermined information.

Figure 3:
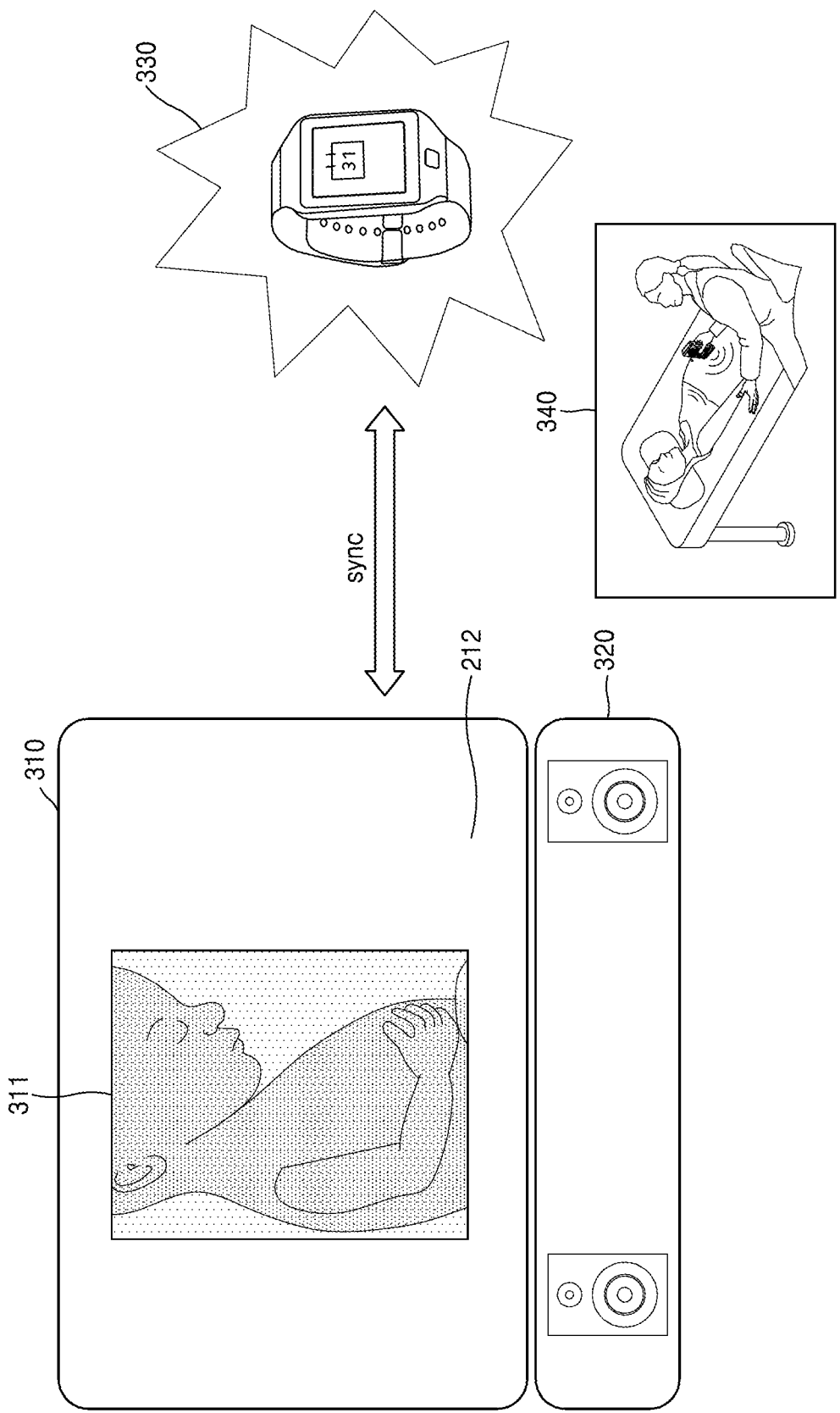
FIG. 3 is a diagram for explaining representation of ultrasound color data via a wearable device.

FIG. 3 is a diagram for explaining representation of an ultrasound color image 311 via a wearable device 330. An ultrasound diagnosis apparatus according to an exemplary embodiment is configured to represent a wearable signal including information obtained based on acquired ultrasound data via the wearable device 330, thereby allowing a user to sense an ultrasound signal through a tactile or auditory sense while viewing the ultrasound color image 311. Thus, this configuration enables a user to conveniently diagnose an object.

For example, according to an exemplary embodiment, both a diagnostician and an examinee may sense a wearable signal through at least one of visual, auditory, and tactile senses. In detail, if a pregnant woman and a doctor wear the wearable device 330, the pregnant woman and the doctor may directly sense information representing a status of her fetus via the wearable device 330 while the doctor performs a diagnostic ultrasound examination 340 of the fetus.

Furthermore, according to an exemplary embodiment, if signals are provided from the ultrasound diagnosis apparatus to the wearable device 330, the wearable device 330 may change a method of generating each signal according to a user's selection. For example, the user may turn on or off a screen 310 or a speaker 320 of the ultrasound diagnosis apparatus, or at least one of vibration, sound, and a screen of the wearable device 330.

Figure 4:
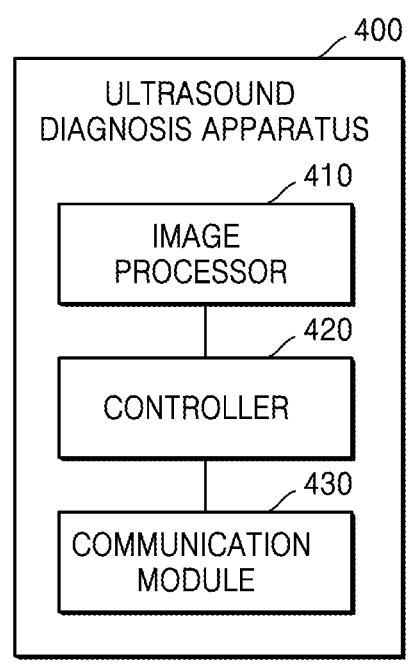
FIG. 4 is a block diagram of a configuration of an ultrasound diagnosis apparatus according to another exemplary embodiment.

FIG. 4 is a block diagram of a configuration of an ultrasound diagnosis apparatus 400 according to another exemplary embodiment.

Referring to FIG. 4, the ultrasound diagnosis apparatus 400 according to the present exemplary embodiment includes an image processor 410, a controller 420, and a communication module 430. The ultrasound diagnosis apparatus 400 may correspond to the ultrasound diagnosis apparatus 1000 of FIG. 1.

The image processor 410 may correspond to the image processor 1200 shown in FIG. 1.

The image processor 410 acquires ultrasound data of an object. The ultrasound data may correspond to an ultrasound echo signal acquired via the probe 20. Furthermore, the ultrasound data may be data generated based on an ultrasound echo signal. For example, the ultrasound data may be ultrasound Doppler data, an ultrasound image, or ultrasound color data. For example, the image processor 410 may acquire ultrasound Doppler data or ultrasound color data related to a fetus via ultrasound examination of a pregnant woman's abdomen. As another example, the image processor 410 may acquire ultrasound Doppler data or ultrasound color data via ultrasound examination of a patient's organ. The ultrasound color data may mean data that may be used to generate an ultrasound color image.

The controller 420 controls overall operations of the ultrasound diagnosis apparatus 400. In detail, the controller 420 produces a wearable signal that has information indicating a difference between acquired ultrasound data and reference ultrasound data. In this case, the reference ultrasound data may include standard ultrasound data and history ultrasound data of an object. The standard ultrasound data may correspond to an average value of values of a plurality of ultrasound data respectively acquired from a plurality of different objects.

A wearable signal may be a signal that can be generated and transmitted by the ultrasound diagnosis apparatus 400 and be received by and output from a wearable device. In detail, the ultrasound diagnosis apparatus 400 may change and generate ultrasound data according to a format of a signal that is processed by the wearable device. For example, if the wearable device is able to recognize or processes an audio signal generated according to a predetermined audio processing standard, the ultrasound diagnosis apparatus 400 may generate a wearable signal having a form of an audio signal that conforms to the predetermined audio processing standard and transmit the wearable signal to the wearable device. As another example, if the wearable device is able to recognize or processes an image signal generated according to a predetermined image processing standard, the ultrasound diagnosis apparatus 400 may generate a wearable signal having a form of an image signal that conforms to the predetermined image processing standard and transmit the wearable signal to the wearable device. Thus, the wearable device may receive a wearable signal and represent the wearable signal by at least one of vibration, an image, and sound from the wearable device.

Standard ultrasound data may be ultrasound data for a normal group of an object. For example, if acquired ultrasound data is ultrasound Doppler data related to the heart of a fetus, the standard ultrasound data may be ultrasound Doppler data related to the heart of a fetus that is selected as belonging to a normal group from among fetuses having the same gestational age. Alternatively, the standard ultrasound data may be average ultrasound Doppler data for fetuses of the same gestational age.

History ultrasound data of an object may be ultrasound data previously acquired from the object. For example, if an ultrasound image of a 20-week old fetus is captured using the ultrasound diagnosis apparatus 400, two ultrasound images of the fetus that were captured at 12-th and 16-th weeks may be history ultrasound data of the fetus.

According to an exemplary embodiment, a wearable signal may be acquired by comparing acquired ultrasound data with reference ultrasound data. Furthermore, the wearable signal may have information indicating a difference between the acquired ultrasound data and the reference ultrasound data, as described in more detail below with reference to FIGS. 6 and 7.

The communication module 430 may correspond to the communication module 1300 shown in FIG. 1.

The communication module 430 transmits a wearable signal generated in the ultrasound diagnosis apparatus 400 to a wearable device.

Furthermore, the communication module 430 may synchronize with the wearable device via a synchronization signal that is periodically transmitted to or received from the wearable device. Synchronizing the ultrasound diagnosis apparatus 400 with the wearable device may mean that the time when an image or audio signal is output from the ultrasound diagnosis apparatus 400 is synchronized with the time when a wearable signal is output from the wearable device. For example, sound and an image of a fetal heartbeat that are obtained using fetal ultrasound Doppler data may be output from the ultrasound diagnosis apparatus 400 and the wearable device at the same time in real-time.

In detail, although the wearable device receives a wearable signal from the ultrasound diagnosis apparatus 400 for output, the wearable device may exchange a synchronization signal with the ultrasound diagnosis apparatus 400 to check the time that the wearable signal was output therefrom.

Figure 5:
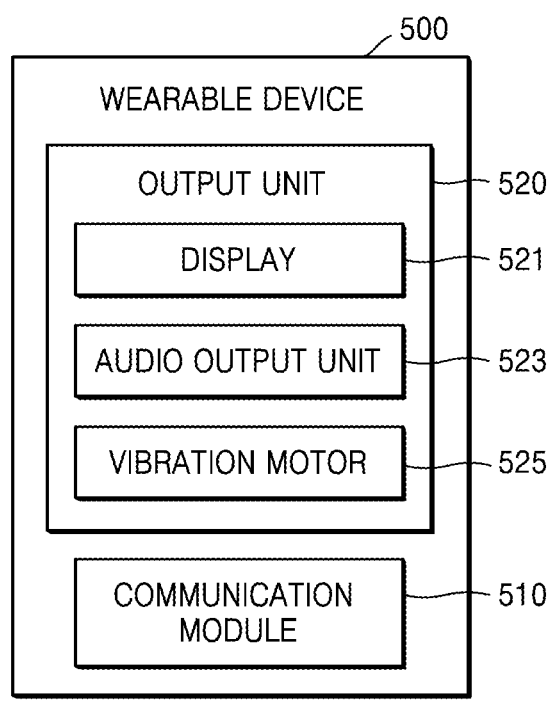
FIG. 5 is a block diagram of a configuration of a wearable device according to an exemplary embodiment.

FIG. 5 is a block diagram of a configuration of a wearable device 500 according to an exemplary embodiment.

Referring to FIG. 5, the wearable device 500 according to the present exemplary embodiment includes a communication module 510 and an output unit 520. The output unit 520 may include at least one of a display 521, an audio output unit 523, and a vibration motor 525.

The wearable device 500 may receive a wearable signal transmitted via the communication module 430 of the ultrasound diagnosis apparatus 400 and convert the wearable signal into at least one of the intensity of vibration, variation in color, and strength of sound to be output.

The communication module 510 of the wearable device 500 may receive a wearable signal generated based on a difference between ultrasound data acquired by the ultrasound diagnosis apparatus 400 and reference ultrasound data.

The wearable device 500 may output a user interface signal corresponding to the difference between the acquired ultrasound data and the reference ultrasound data via the output unit 520 based on the wearable signal.

The display 521 included in the output unit 520 may output a screen that depicts a wearable signal as a variation in color on the basis of a difference between acquired ultrasound data and reference ultrasound data. For example, a color value difference for each region may be depicted as a color by comparing ultrasound color data for the acquired ultrasound data with ultrasound color data for the reference ultrasound data, as described in more detail below with reference to FIG. 7.

The audio output unit 523 included in the output unit 520 may output an audio signal representing a wearable signal as strength of sound based on a difference between acquired ultrasound data and reference ultrasound data, as described in more detail with reference to FIG. 6.

The vibration motor 525 included in the output unit 520 may output vibration that has varying intensity according to a wearable signal, based on a difference between acquired ultrasound data and reference ultrasound data.

The output unit 520 will be described in more detail below with reference to FIGS. 10 and 11.

Figure 6:
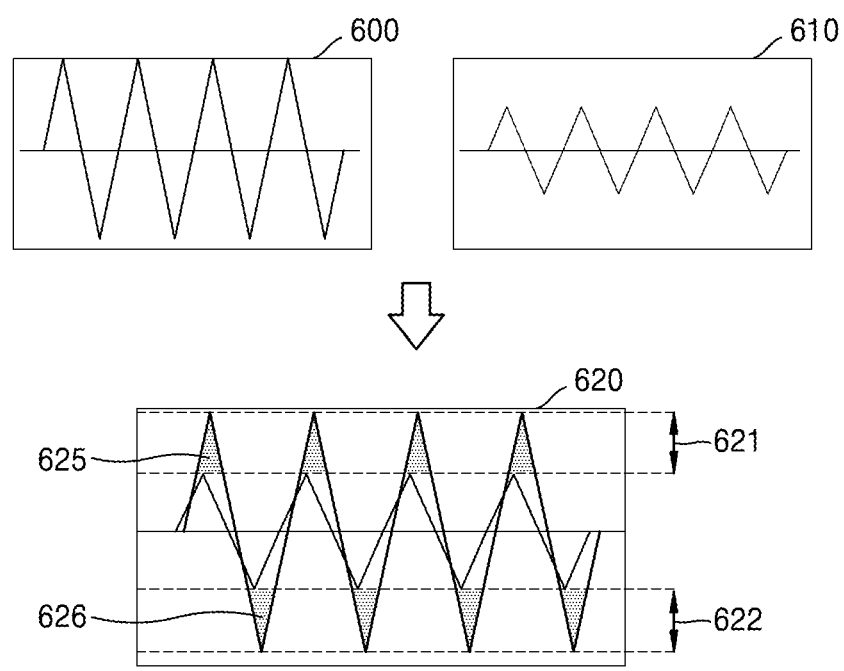
FIG. 6 is a diagram for explaining a signal generated based on a difference between reference ultrasound data and acquired ultrasound data

FIG. 6 is a diagram for explaining a signal generated based on a difference between reference ultrasound data and acquired ultrasound data. In detail, FIG. 6 is a diagram for explaining generation of a wearable signal.

According to an exemplary embodiment, the image processor 410 of the ultrasound diagnosis apparatus 400 may acquire ultrasound Doppler data of an object. It is assumed hereinafter that ultrasound data acquired by the image processor 410 is ultrasound Doppler data.

According to an exemplary embodiment, the controller 420 of the ultrasound diagnosis apparatus 400 may compare first Doppler spectrum data corresponding to acquired ultrasound Doppler data with second Doppler spectrum data corresponding to reference ultrasound data, thereby generating a wearable signal based on a difference between values of the first and second Doppler spectrum data. In this case, a value of Doppler spectrum data may be one particular value contained in the Doppler spectrum data. For example, the value of Doppler spectrum data may be a maximum value, a minimum value, or a peak value (if converted into a graph) of the Doppler spectrum data.

For example, the controller 420 of the ultrasound diagnosis apparatus 400 may compare a first graph 600 representing a Doppler spectrum obtained from acquired ultrasound Doppler data with a second graph 610 representing a Doppler spectrum obtained from reference ultrasound data, thereby generating a wearable signal that has information indicating differences between at least one peak value in the first graph 600 and at least one peak value in the second graph 610.

Referring to FIG. 6, the first and second graphs 600 and 610 represent Doppler spectra respectively obtained from reference ultrasound Doppler data and acquired ultrasound Doppler data of an object.

A third graph 620 is created by comparing the first and second graphs 600 and 610 with each other. For example, the third graph 620 may be created based on the differences between the at least one peak value in the first graph 600 and the at least one peak value in the second graph 610. In detail, heights 621 and 622 of oblique lined portions 625 and 626 represent differences between each of the peak values in the first and second graphs 600 and 610. While FIG. 6 is an example where differences between each of the peak values in the first graph 600 are equal to a corresponding peak value in the second graph 610, the differences may vary according to a difference between acquired ultrasound Doppler data of the object and reference ultrasound Doppler data.

According to an exemplary embodiment, the controller 420 of the ultrasound diagnosis apparatus 400 may adjust the intensity of a wearable signal based on differences between peak values. In detail, the wearable device 500 may output sound, color, or vibration having intensity that is proportional to a difference between peak values in the first and second graphs 600 and 610. For example, if a difference between each peak value in the first graph 600 and a corresponding peak value in the second graph 610 is small, the wearable device 500 may output vibration having low intensity that is proportional to the difference. On the other hand, if the difference is large, the wearable device 500 may output vibration having high intensity that is proportional to the difference.

According to an exemplary embodiment, the controller 420 of the ultrasound diagnosis apparatus 400 may determine an examination required for an object based on differences between peak values and display the determined examination on the wearable device.

For example, if an absolute value of a difference between peak values exceeds a predetermined value, the controller 420 of the ultrasound diagnosis apparatus 400 may determine that there is an abnormality in the object and thus determine examinations required regarding the abnormality. In detail, if the first graph 600 represents a Doppler spectrum of the heart of a fetus in a normal group, and the second graph 610 represents a Doppler spectrum of the heart of a fetus as an object, a difference between peak values in the first and second graphs 600 and 610 may exceed a predetermined value. In this case, the ultrasound diagnosis apparatus 400 may inform a user that the fetus has a heartbeat that is weaker or extremely stronger than an average heartbeat of a fetus and suggest a required examination to the user.

Furthermore, according to another exemplary embodiment, the controller 420 of the ultrasound diagnosis apparatus 400 may determine an examination required for the object based on a difference between periods in the first and second graphs 600 and 610 and display the determined examination on the wearable device 500.

For example, if the first graph 600 represents a Doppler spectrum of the heart of a fetus as an object and the second graph 610 represents a Doppler spectrum of the heart of a fetus in a normal group, a difference between periods in the first and second graphs 600 and 610 may exceed a predetermined value. In this case, the ultrasound diagnosis apparatus 400 may inform a user that the fetus is under stress and suggest a required examination.

According to an exemplary embodiment, if at least one of differences between peak values in the first and second graphs 600 and 610 exceeds a predetermined reference value, the controller 420 of the ultrasound diagnosis apparatus 400 may control the wearable device 500 to generate an alarm that will be then provided to the user via a sound, vibration, or screen.

For example, if a difference between peak values at a time point when the peak values occur exceeds a predetermined reference value, the controller 420 of the ultrasound diagnosis apparatus 400 may control the wearable device 500 to generate vibration. In this case, the user may sense the vibration via the wearable device 500 each time the difference exceeds the predetermined reference value.

Furthermore, the controller 420 of the ultrasound diagnosis apparatus 400 may compare periods in the first and second graphs 600 and 610 with each other. In this case, if a difference between the periods in the first and second graphs 600 and 610 exceeds a predetermined reference value, the controller 410 of the ultrasound diagnosis apparatus 400 may control the wearable device 500 to generate an alarm sound that may inform the user that there is a problem in a period of an ultrasound wave from an object.

Furthermore, the wearable device 500 may represent highest/lowest peaks of a Doppler signal as strong/weak vibration by using the first graph 600 representing a Doppler spectrum obtained from acquired ultrasound Doppler data. Furthermore, the wearable device 500 may represent highest/lowest peaks of a Doppler signal as a variation in color by using the first graph 600. For example, the wearable device 500 may output a red color at the highest peak of the Doppler signal and a blue color at the lowest peak thereof.

Although FIG. 6 shows the first and second graphs 600 and 610 as examples of Doppler spectra, exemplary embodiments are not limited thereto. For example, Doppler spectrum data may be compared with each other as described above without being converted into graphs.

Figure 7:
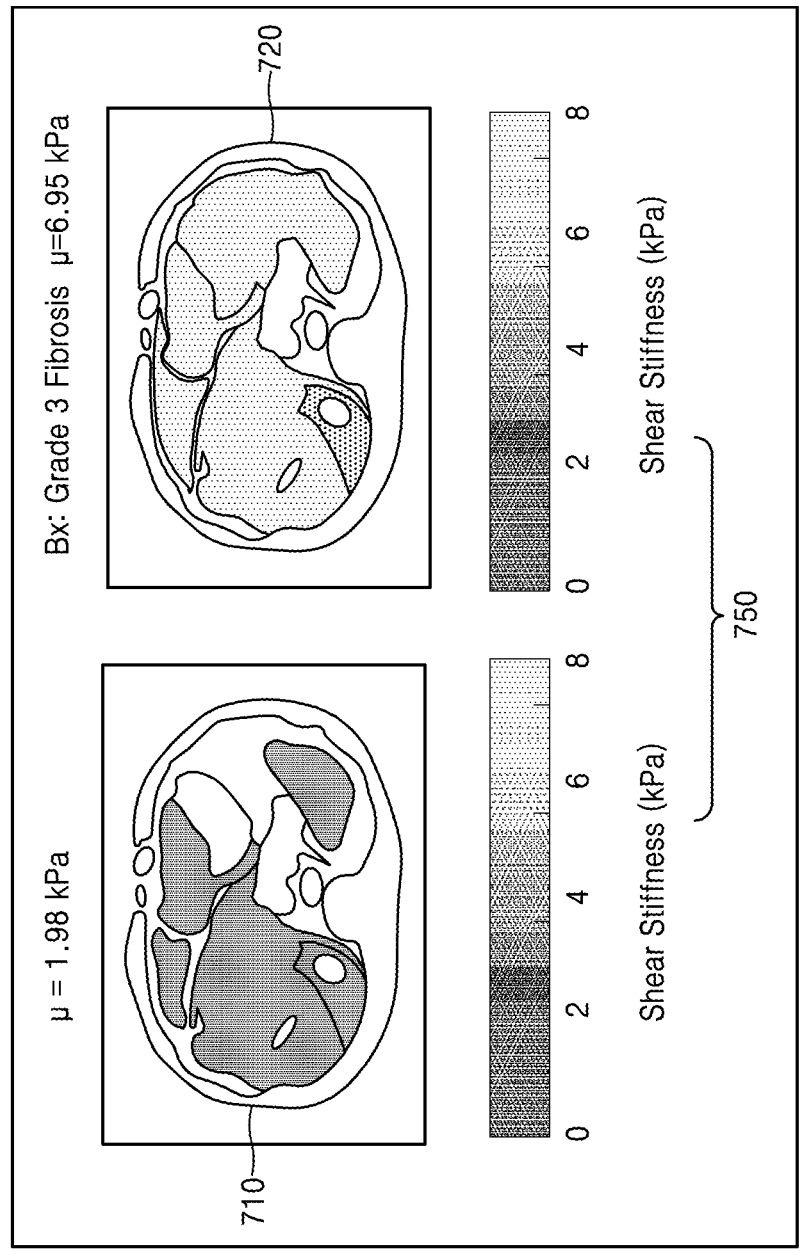
FIG. 7 illustrates a comparison between elastography images showing tissue stiffness.

FIG. 7 illustrates a comparison between elastography images showing tissue stiffness.

According to an exemplary embodiment, the image processor 410 of the ultrasound diagnosis apparatus 400 may acquire ultrasound color data of an object. In this case, the controller 420 may compare an ultrasound color image generated based on the acquired ultrasound color data with a predetermined ultrasound color image, thereby generating a wearable signal based on a difference between colors of the ultrasound color images.

According to an exemplary embodiment, the controller 420 may control the wearable device 500 to display the acquired ultrasound color data in a color corresponding to the difference between colors.

Referring to FIGS. 7, 710 and 720 respectively represent elastography images of reference ultrasound color data and ultrasound color data of an object.

In detail, the elastography images 710 and 720 respectively depict a healthy person's liver and the object.

As seen on FIG. 7, the elastography image 710 of the healthy person's liver shows a shear stiffness value of 1.98 kilopascals (kPa), and the elastography image 720 of the object shows a shear stiffness value of 6.95 kPa, which is higher than that of the healthy person's liver.

In this case, the ultrasound diagnosis apparatus 400 may transmit 3.97 kPa that is a difference between the shear stiffness values shown in the elastography images 710 and 720 to the wearable device 500.

Furthermore, according to an exemplary embodiment, if a value corresponding to a difference between colors exceeds a predetermined reference value, the ultrasound diagnosis apparatus 400 may control the wearable device 500 to generate an alarm. In this case, the alarm may be in the form of sound, an image, or vibration.

The ultrasound diagnosis apparatus 400 may also generate new elastography data having a color corresponding to a difference between stiffness values of regions in the elastography image 710 of reference ultrasound color data and the elastography image 720 of ultrasound color data of the object.

For example, the new elastography data may be visually represented for the user on a display of the wearable device 500. In detail, if a difference between stiffness values of regions in the elastography images 710 and 720 is greater than a predetermined value, each region in the new elastography data displayed on the wearable device 500 may be represented in red. On the other hand, if the difference is less than or equal to the predetermined value, a corresponding region may be represented in blue. Selection of these colors is merely an example, and exemplary embodiments are not limited thereto.

A difference in tissue stiffness may be represented using at least one of the intensity of variation and variation in color. For example, if the difference in tissue stiffness is large, the wearable device 500 may generate vibration having a high intensity or represent the difference in tissue stiffness in a deeper color.

Figure 8:
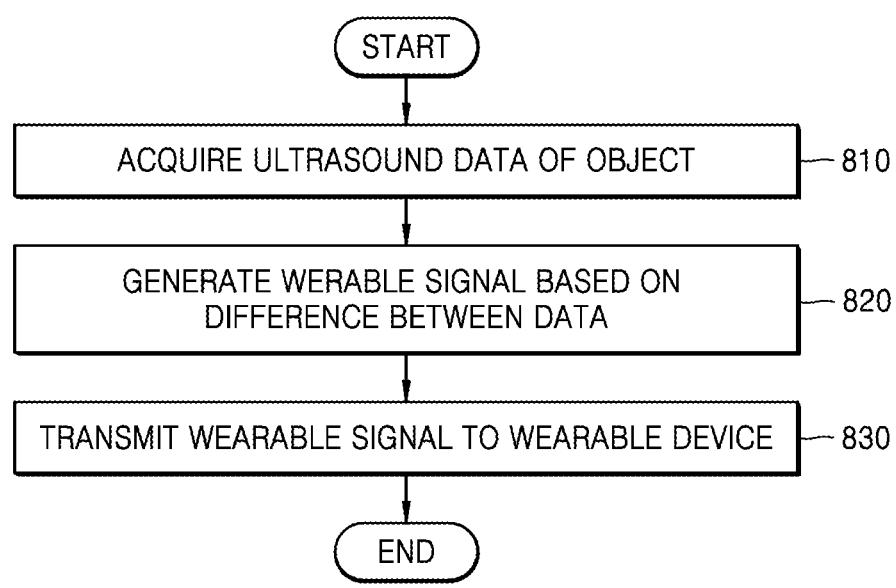
FIG. 8 is a flowchart of a method of controlling an ultrasound diagnosis apparatus according to an exemplary embodiment.

FIG. 8 is a flowchart of a method of controlling the ultrasound diagnosis apparatus 400, according to an exemplary embodiment.

Referring to FIGS. 4, 5, and 8, the image processor 410 of the ultrasound diagnosis apparatus 400 acquires ultrasound data of an object (operation 810).

The controller 420 generates a wearable signal that is to be output from the wearable device 500 based on a difference between acquired ultrasound data and predetermined ultrasound data (operation 820).

The communication module 430 may transmit the wearable signal to the wearable device 500 (operation 830).

According to an exemplary embodiment, the ultrasound diagnosis apparatus 400 may control a difference between ultrasound data of the object and reference ultrasound data to be displayed on the wearable device 500. Furthermore, the ultrasound diagnosis apparatus 400 may control a difference between previously generated history data of the object and current ultrasound data of the object to be displayed on the wearable device 500.

According to an exemplary embodiment, the wearable device 500 allows the user to recognize a signal intensity by sensing at least one of vibration and sound without viewing a screen.

According to an exemplary embodiment, the ultrasound diagnosis apparatus 400 may transmit a signal generated from a fetus, e.g., the fetus's heart rate, simultaneously to a plurality of wearable devices 500.

According to an exemplary embodiment, the wearable device 500 may automatically adjust the intensity of a signal (vibration, sound, and image represented thereon according to the magnitude of a signal representing a difference between values for reference ultrasound data and acquired ultrasound data.

According to an exemplary embodiment, the ultrasound diagnosis apparatus 400 may determine an item requiring examination according to the magnitude of a signal representing a difference between values for reference ultrasound data and acquired ultrasound data and transmit the item to the wearable device 500.

In this case, the wearable device 500 may inform the user of an item requiring examination by displaying the item on a display thereof.

Furthermore, the ultrasound diagnosis apparatus 400 may analyze the periodicity of a fetus's heartbeat, quantify a stress level of the fetus, and provide the stress level of the fetus to the user. In addition, the ultrasound diagnosis apparatus 400 may analyze the periodicity of a fetus's heartbeat and provide the result of the analysis to the user as a sensory signal. For example, if the periodicity of the fetus's heartbeat is abnormal, the ultrasound diagnosis apparatus 400 may represent the abnormal periodicity as vibration and provide the vibration to the user, thereby allowing a user to recognize that the fetus has a high stress level.

Figure 9:
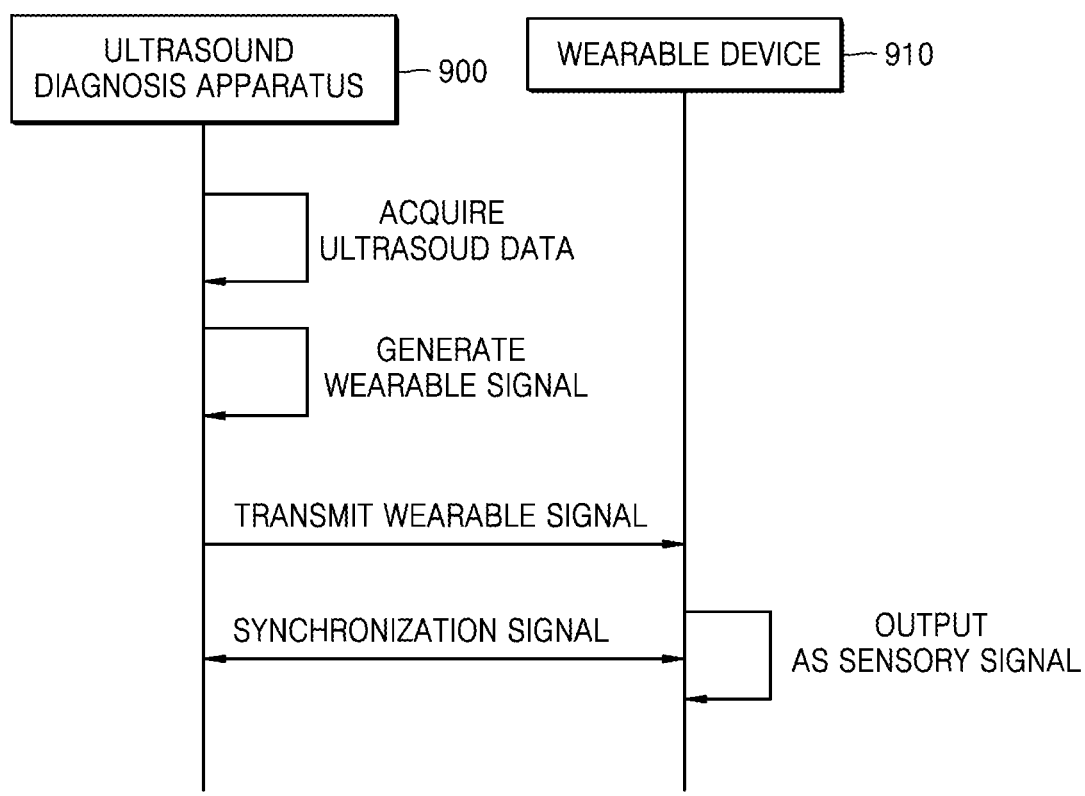
FIG. 9 is a diagram for explaining exchange of signals between an ultrasound diagnosis apparatus and a wearable device.

FIG. 9 is a diagram for explaining exchange of signals between an ultrasound diagnosis apparatus 900 and a wearable device 910.

The ultrasound diagnosis apparatus 900 may acquire ultrasound data from an object. Then, the ultrasound diagnosis apparatus 900 may generate a wearable signal to be transmitted to the wearable device 910. The wearable signal may be generated by comparing acquired ultrasound data against reference ultrasound data.

The ultrasound diagnosis apparatus 900 may transmit the generated wearable signal to the wearable device 910.

The wearable device 910 may output the received wearable signal as a sensory signal and provide the sensory signal to the user.

In this case, the ultrasound diagnosis apparatus 900 may exchange a synchronization signal with the wearable device 910 in order to synchronize a sensory signal output from by the wearable device 910 with an ultrasound signal represented via a display or speaker of the ultrasound diagnosis apparatus 900.

Figure 10:
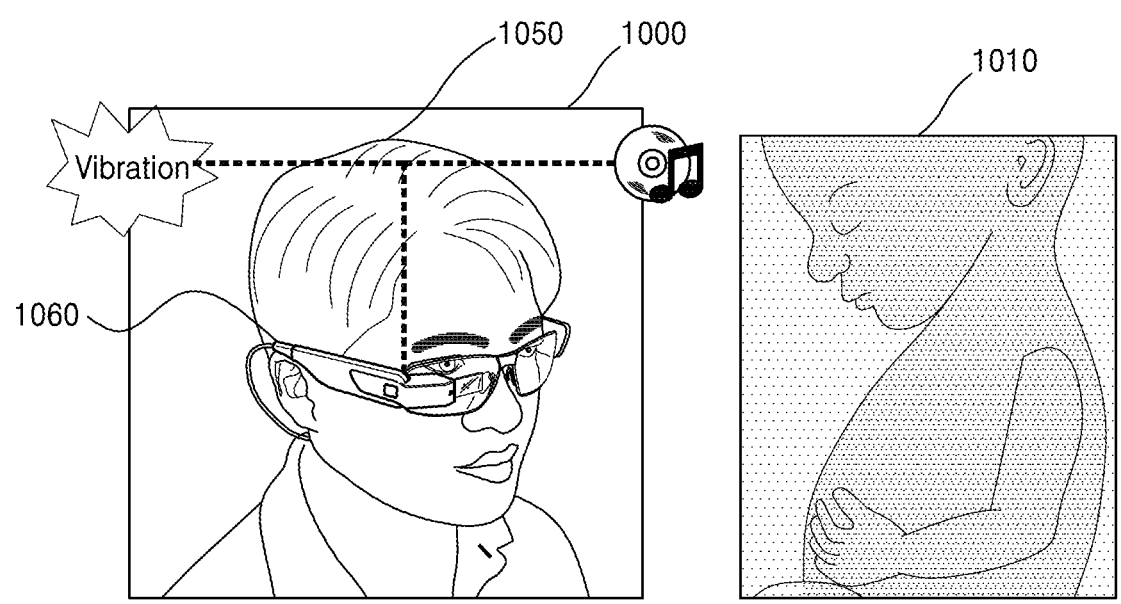
FIG. 10 is a diagram for explaining a form in which a wearable signal is output via an output unit of a wearable device.

FIG. 10 is a diagram for explaining a form in which a wearable signal is output via an output unit of smart glasses 1060 that is an example of the wearable device 500.

According to an exemplary embodiment, the wearable device 500 may output a user interface signal corresponding to a difference between ultrasound data acquired by the ultrasound diagnosis apparatus (400 of FIG. 4) and reference ultrasound data, based on a wearable signal generated based on the difference.

According to an exemplary embodiment, the wearable device 500 may receive a wearable signal transmitted from the communication module (430 of FIG. 4) and convert the wearable signal into a variation in color to be output.

Referring to FIG. 10, a user 1050 is wearing the smart glasses 1060 that is an example of the wearable device 500.

For example, the smart glasses 1060 may provide a color ultrasound image 1010 of a fetus to the user 1050 via a display.

According to an exemplary embodiment, the smart glasses 1060 may receive a wearable signal transmitted from the communication module 430 and convert the wearable signal into sound having certain strength to be output).

For example, a fetal heartbeat sound may be provided to the user 1050 via an audio output unit of the smart glasses 1060.

According to an exemplary embodiment, the smart glasses 1060 may receive a wearable signal transmitted from the communication module 430 and convert the wearable signal into intensity of vibration to be output. For example, the smart glasses 1060 may convert a fetal heartbeat into vibration and provide the vibration to the user 1050 via a vibration motor.

FIGS. 11A through 11D are a diagram for explaining conversion of a signal generated based on a difference between acquired ultrasound data and reference ultrasound data into a user interface signal.

Figure 11A:
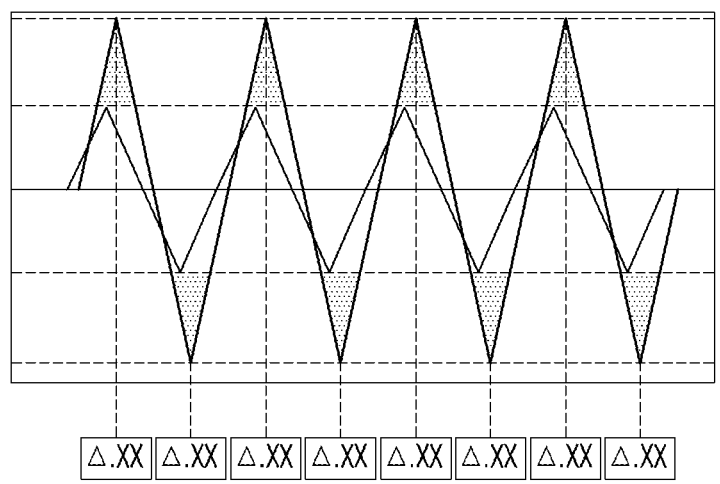
FIGS. 11A through 11D are a diagram for explaining conversion of a signal generated based on a difference between acquired ultrasound data and reference ultrasound data into a user interface signal.

FIG. 11A illustrates a difference between first and second graphs respectively representing Doppler spectra corresponding to acquired ultrasound Doppler data and reference ultrasound data. To obtain the difference, the controller 420 of the ultrasound diagnosis apparatus 400 may compare the first and second graphs with each other.

Figure 11B:
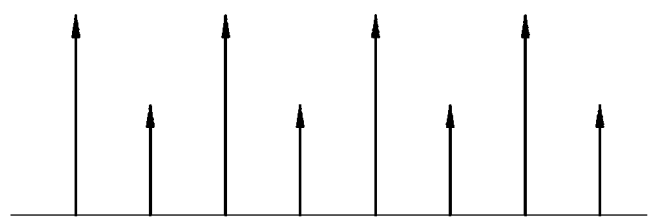

FIG. 11B illustrates a wearable signal generated based on differences between at least one peak value in the first graph and at least one peak value in the second graph. For example, the magnitude of the wearable signal may be determined based on a value corresponding to a difference between each of peak values in the first and second graphs. Referring to FIG. 11B, the wearable signal is composed of high- and low-amplitude sound waves that appear alternately.

Figure 11C:
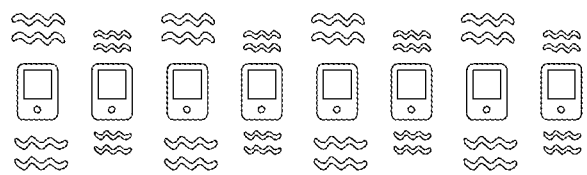

FIG. 11C illustrates vibration generated by the wearable device 500 based on a wearable signal. Referring to FIG. 11C, high- and low-intensity vibrations occur alternately according to the magnitude of the wearable signal.

Figure 11D:
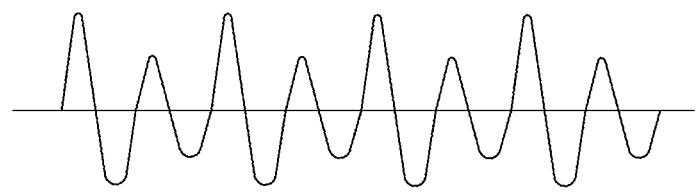

FIG. 11D illustrates sound generated by the wearable signal 500 based on a wearable signal. Referring to FIG. 11D, the sound based on the wearable signal is represented as a sound pitch. In addition, the sound may be output as strength thereof.

The exemplary embodiments may be written as computer programs and may be implemented in general-use digital computers that execute the programs using a computer-readable recording medium.

Computer-readable media may be any available media that can be accessed by a computer and include both volatile and nonvolatile media and both detachable and non-detachable media. Furthermore, the computer-readable media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and they include any information transmission media.

The above description is provided for illustration, and it will be understood by those of ordinary skill in the art that various changes in form and details may be made therein without departing from essential features and the spirit and scope of the present inventive concept as defined by the following claims. Accordingly, the above embodiments and all aspects thereof are examples only and are not limiting. For example, each component defined as an integrated component may be implemented in a distributed fashion. Likewise, components defined as separate components may be implemented in an integrated manner.

The scope of the present inventive concept is defined not by the detailed description thereof but by the appended claims, and all the changes or modifications within the scope of the appended claims and their equivalents will be construed as being included in the present inventive concept.

What is claimed is:

1. An ultrasound diagnosis apparatus comprising:
an image processor configured to acquire ultrasound data of an object, the acquired ultrasound data comprising ultrasound Doppler data;
a controller configured to:
compare first Doppler spectrum data corresponding to the ultrasound Doppler data with second Doppler spectrum data corresponding to reference ultrasound data,
generate, based on differences between values of the first and second Doppler spectrum data, a wearable signal for controlling a wearable device such that the wearable device can convert the wearable signal into an intensity of vibration and output a result obtained by the conversion,
adjust an amplitude of the wearable signal for controlling the wearable device, based on the differences between the values of the first and second Doppler spectrum data, to adjust the intensity of vibration, wherein the wearable signal carries information corresponding to a difference between the acquired ultrasound data and the reference ultrasound data,
synchronize with the wearable device via a synchronization signal, so that a time when an image or audio signal related to the object is output from the ultrasound diagnosis apparatus is synchronized with a time when the wearable device outputs the intensity of vibration, and
if at least one of the differences between the values of the first and second Doppler spectrum data is greater than a first predetermined reference value, determine at least one abnormality in the object based on the differences between the values of the first and second Doppler spectrum data, generate information suggesting at least one examination with regard to the at least one abnormality, and control the wearable device to display the information suggesting the at least one examination with regard to the at least one abnormality; and
a communicator configured to transmit the wearable signal and the information suggesting the at least one examination with regard to the at least one abnormality to the wearable device,
wherein the synchronization signal is periodically transmitted to and received by the wearable device, by the ultrasound diagnosis apparatus controlling the communicator.

2. The ultrasound diagnosis apparatus of claim 1, wherein the controller is further configured to determine an item of the object that requires examination based on the differences between the values of the first and second Doppler spectrum data and controls the wearable device to display the determined item.

3. The ultrasound diagnosis apparatus of claim 1, wherein if at least one of the differences between the values of the first and second Doppler spectrum data is greater than a second predetermined reference value, the controller is further configured to control the wearable device to generate an alarm.

4. The ultrasound diagnosis apparatus of claim 1,
wherein the controller is further configured to compare a period in a first graph representing the first Doppler spectrum with a period in a second graph representing the second Doppler spectrum and, if a difference between the periods in the first and second graphs exceeds a second predetermined reference value, the controller is further configured to control the wearable device to generate an alarm.

5. The ultrasound diagnosis apparatus of claim 1,
wherein the image processor acquires ultrasound color data for generating a color ultrasound image of the object;
wherein the controller is further configured to generate a color-encoded wearable signal for controlling the wearable device such that the wearable device can convert the color-encoded wearable signal into a variation in color and output a result obtained by the conversion,
wherein the color-encoded wearable signal carries information corresponding to a difference in color between the acquired ultrasound color data and predetermined ultrasound color data; and
wherein the controller is further configured to control the wearable device to display the color data in a color corresponding to the difference in color between the acquired ultrasound color data and the predetermined ultrasound color data.

6. The ultrasound diagnosis apparatus of claim 5, wherein, if a value corresponding to the difference in color data is greater than a second predetermined reference value, the controller is further configured to control the wearable device to generate an alarm.

7. The ultrasound diagnosis apparatus of claim 1, wherein the reference ultrasound data comprises standard ultrasound data and history ultrasound data of the object, wherein the standard ultrasound data corresponds to an average data of a plurality of ultrasound data respectively acquired from a plurality of different objects.

8. The ultrasound diagnosis apparatus of claim 1, further comprising the wearable device, wherein the wearable device is configured to receive the wearable signal transmitted from the communicator, convert the wearable signal into the intensity of vibration, and output the result obtained by the conversion.

9. The ultrasound diagnosis apparatus of claim 1, wherein the ultrasound data of the object further comprises ultrasound color data, or motion (M) mode ultrasound data of the object.

10. A method of controlling an ultrasound diagnosis apparatus, the method comprising:
acquiring ultrasound data of an object, the acquired ultrasound data comprising ultrasound Doppler data;
comparing first Doppler spectrum data corresponding to the ultrasound Doppler data with second Doppler spectrum data corresponding to reference ultrasound data;
generating, based on differences between values of the first and second Doppler spectrum data, a wearable signal for controlling a wearable device such that the wearable device can convert the wearable signal into intensity of vibration and output a result obtained by the conversion,
adjusting an amplitude of the wearable signal for controlling the wearable device, based on the differences between the values of the first and second Doppler spectrum data, to adjust the intensity of vibration, wherein the wearable signal carries information corresponding to a difference between the acquired ultrasound data and the reference ultrasound data; and
synchronizing with the wearable device via a synchronization signal, so that a time when an image or audio signal related to the object is output from the ultrasound diagnosis apparatus is synchronized with a time when the wearable device outputs the intensity of vibration; and
determining that at least one of the differences between the values of the first and second Doppler spectrum data is greater than a first predetermined reference value, determining at least one abnormality in the object based on the differences between the values of the first and second Doppler spectrum data, generating information suggesting at least one examination with regard to the at least one abnormality, transmitting the wearable signal and the information suggesting the at least one examination with regard to the at least one abnormality to the wearable device, and controlling the wearable device to display the information suggesting the at least one examination with regard to the at least one abnormality,
wherein the synchronization signal is periodically transmitted to and received by the wearable device, by the ultrasound diagnosis apparatus controlling a communicator.

11. The method of claim 10, further comprising:
determining an item of the object that requires examination based on the differences between the values of the first and second Doppler spectrum data; and
controlling the wearable device to display the determined item.

12. The method of claim 10, further comprising, determining that at least one of the differences between the values of the first and second Doppler spectrum data is greater than a second predetermined reference value, and controlling the wearable device to generate an alarm.

13. The method of claim 10,
wherein the generating of the wearable signal comprises:
comparing a period in a first graph representing the first Doppler spectrum with a period in a second graph representing the second Doppler spectrum; and
controlling the wearable device to generate an alarm based on determining that a difference between the periods in the first and second graphs exceeds a second predetermined reference value.

14. The method of claim 10,
wherein the acquiring of the ultrasound data of the object comprises acquiring ultrasound color data for generating a color ultrasound image of the object;
wherein the generating of the wearable signal comprises generating a color-encoded wearable signal for controlling the wearable device such that the wearable device can convert the color-encoded wearable signal into a variation in color and output a result obtained by the conversion, wherein the color-encoded wearable signal carries information corresponding to a difference in color between the acquired ultrasound color data and predetermined ultrasound color data; and
controlling the wearable device to display the color data in a color corresponding to the difference in color between the acquired ultrasound color data and the predetermined ultrasound color data.

15. The method of claim 14, wherein the generating of the wearable signal further comprises, determining that a value corresponding to the difference in color data is greater than a second predetermined reference value, and controlling the wearable device to generate an alarm.

16. The method of claim 10, wherein the reference ultrasound data comprises standard ultrasound data and history ultrasound data of the object wherein the standard ultrasound data corresponds to an average data of a plurality of ultrasound data respectively acquired from a plurality of different objects.

17. The method of claim 10, further comprising:
receiving the wearable signal at the wearable device; and
controlling the wearable device to convert the wearable signal into the intensity of vibration, and outputting the result obtained by the conversion.

18. A non-transitory computer-readable recording medium having recorded thereon a program for executing the method of any one of claims 10, 11-14 and 15-17 on a computer.

* * * * *